United States Patent [19]

Schiessler et al.

[11] Patent Number: 4,599,431
[45] Date of Patent: Jul. 8, 1986

[54] PROCESS FOR THE PREPARATION OF NAPHTHALENE-1,4,5,8-TETRACARBOXYLIC ACID AND ITS 1,8-MONOANHYDRIDE IN A HIGH DEGREE OF PURITY

[75] Inventors: Siegfried Schiessler, Bad Soden am Taunus; Ernst Spietschka, Idstein, both of Fed. Rep. of Germany

[73] Assignee: Hoechst Aktiengesellschaft, Frankfurt am Main, Fed. Rep. of Germany

[21] Appl. No.: 627,776

[22] Filed: Jul. 5, 1984

[30] Foreign Application Priority Data

Jul. 9, 1983 [DE] Fed. Rep. of Germany ....... 3324881

[51] Int. Cl.$^4$ ........................................... C07D 311/80
[52] U.S. Cl. .................................... 549/232; 562/480; 562/485; 562/486
[58] Field of Search ................ 549/232; 562/480, 485, 562/486

[56] References Cited

U.S. PATENT DOCUMENTS 3,628,976 12/1971 Stocker .......................... 549/232 X
4,355,175 10/1982 Pusztaszeri ..................... 562/485 X
4,501,906 2/1985 Spietschka et al. ................. 549/232

FOREIGN PATENT DOCUMENTS 0073464 5/1985 European Pat. Off. .

OTHER PUBLICATIONS

Chemical Abstracts, vol. 98, No. 20 (1983)—p. 4, Compilation 98:161 239.
Russian Chemical Reviews (Nov. 1965), vol. 34, No. 11, pp. 829–830.

Primary Examiner—Richard L. Raymond
Attorney, Agent, or Firm—Connolly and Hutz

[57] ABSTRACT

Process for the preparation of naphthalene-1,4,5,8-tetracarboxylic acid (called "NTC" below) and its 1,8-monoanhydride in a high degree of purity, which comprises dissolving impure NTC or impure NTC-1,8-monoanhydride as the tetra-alkali metal salt of NTC in water in known manner, removing any insoluble impurities present, bringing the clarified solution to a pH value of 4–5 below 45° C., separating off the di-alkali metal salt of NTC which thereby crystallizes out and converting the latter into free NTC or into free NTC-1,8-monoanhydride by treatment with a strong acid at 20° to 100° C.

8 Claims, 2 Drawing Figures

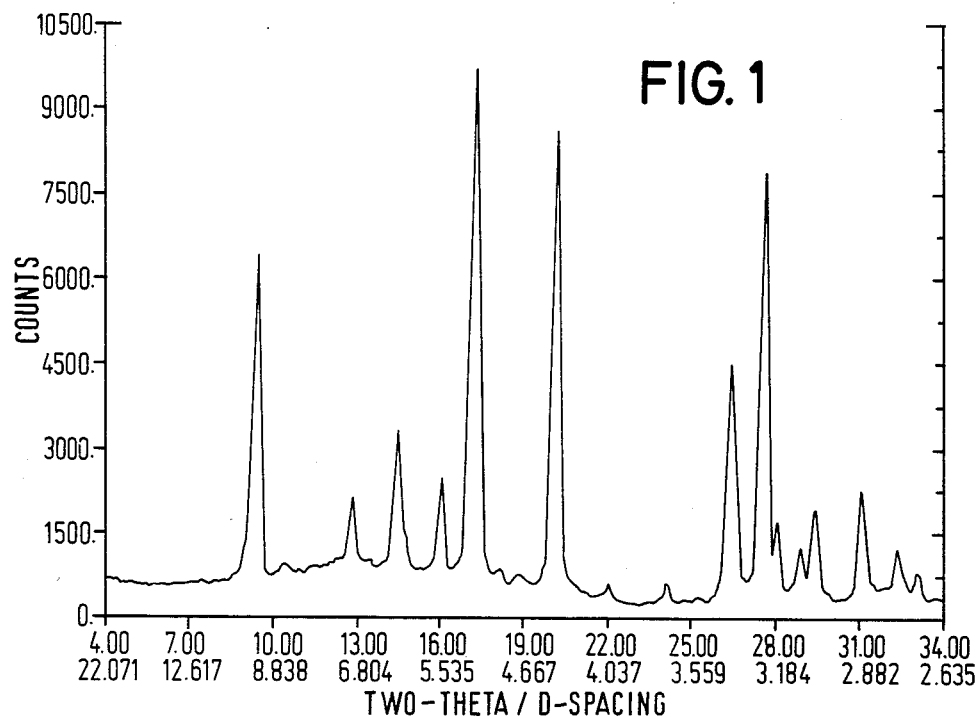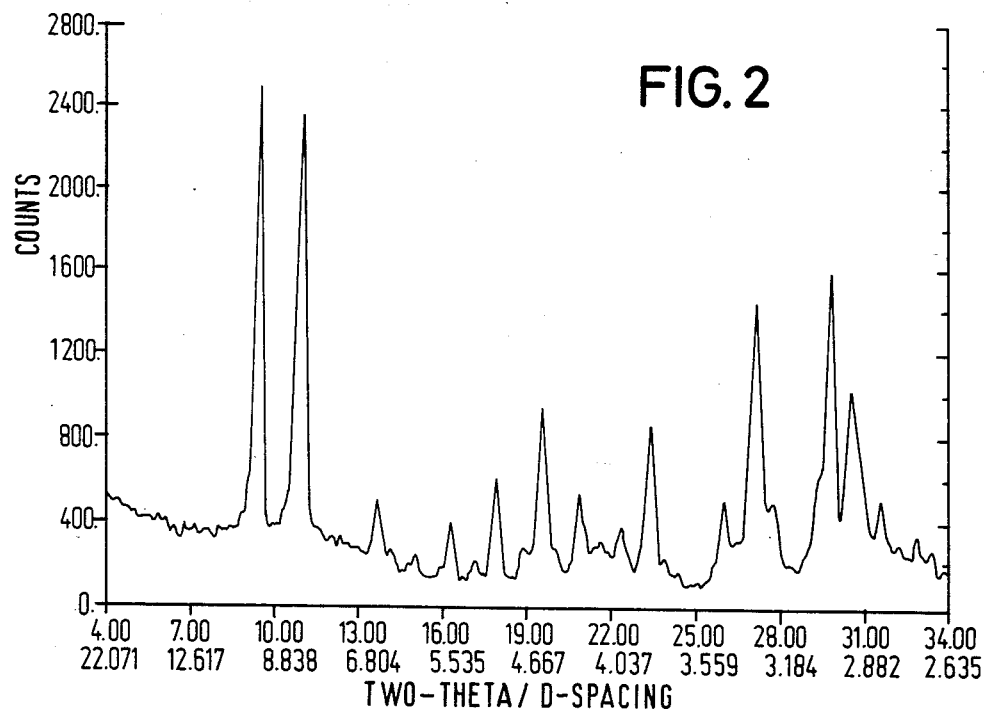

PROCESS FOR THE PREPARATION OF NAPHTHALENE-1,4,5,8-TETRACARBOXYLIC ACID AND ITS 1,8-MONOANHYDRIDE IN A HIGH DEGREE OF PURITY

Naphthalene-1,4,5,8-tetracarboxylic acid (called "NTC" below) (formula I) is an important organic intermediate for the preparation of dyestuffs and pigments. When prepared industrially, NTC is usually obtained in the form of its 1,8-monoanhydride (formula II) and, at very high drying temperatures, also as the dianhydride (formula III).

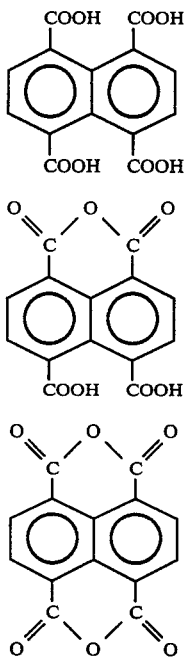

The usual starting substance at present for the preparation of NTC is technical grade pyrene, which is obtained on distillation of coal tar. The preparation process for NTC described in Fiat Final Report 1313 II, which uses acenaphthene as the starting substance, no longer has substantial industrial importance. As is known (cf., for example, Russian Chem. Rev. 34 (1965), pages 829-830), the preparation of NTC from pyrene can be carried out either by direct oxidation or by the roundabout route via 1,3,6,8-tetrahalogenopyrene. In this second synthesis route, pyrene is first converted into the 1,3,6,8-tetrahalogenopyrene by chlorination or bromination, and this is converted into 1,2,3,6,7,8-hexahydro-1,3,6,8-pyrenetetrone or its 2,7-dibromo derivative (in the case of tetrabromopyrene) by oxidative dehalogenation in oleum. NTC can be obtained from these two products either by acid or alkaline oxidation.

The NTC obtained by the various possible known synthesis processes is as a rule still considerably impure. This is initially to be attributed to the fact that by-products are formed in the course of the synthesis as a result of side reactions or incomplete conversion. As main reason, however, is also that technical grade pyrene contains only about 90-95% of pyrene. The remainder consists of polycyclic compounds, the structure of which is known in some cases (for example β-brasane or fluoroanthene) and unknown in other cases, these compounds likewise resulting in secondary reactions, which lead to contamination of the NTC, in the context of the preparation of NTC. 100% pure pyrene cannot be obtained in an economical manner by distillation because of the very similar vapor pressure of the polycyclic impurities. Although purification of pyrene by recrystallization is possible, it means an unacceptable expenditure because of the pyrene losses which thereby arise.

If the impurities which are obtained in the preparation of NTC are insoluble in dilute alkali metal hydroxide solution, they can be removed relatively easily by dissolving the impure NTC in the form of the tetraalkali metal salt in aqueous alkali metal solution and removing the insoluble impurities by filtration. The same of course also applies if the NTC occurs in the form of an aqueous solution of its tetra-alkali metal salt in the context of the synthesis process (for example in an alkaline oxidation process). However, some of the impurities are likewise soluble in an aqueous-alkaline medium and can therefore not be removed in the context of the filtration. If the NTC is precipitated, as described in Fiat Final Report 1313, by acidification of the aqueous solution of the tetra-alkali metal salt of NTC, experience shows that the impurities are also precipitated at the same time. The NTC and/or its anhydrides are therefore obtained in a purity of only 85-95%, depending on the synthesis method.

However, it is extremely important that very highly pure NTC is used for the preparation of dyestuffs and pigments based on NTC. If impure NTC is used, experience has shown that a number of dyestuffs and pigment properties, such as, for example, the purity of the color shade, are very adversely affected.

It has been found that naphthalene-1,4,5,8-tetracarboxylic acid (called "NTC" below) and its 1,8-monohydride can be obtained in a high degree of purity (98-100% purity) by dissolving impure NTC or impure NTC-1,8-monoanhydride as the tetra-alkali metal salt of NTC in water in known manner, removing any insoluble impurities present, advantageously by filtration, acidifying the clarified aqueous solution to a pH value of 4-5 below 45° C., separating off the sparingly soluble di-alkali metal salt of NTC which thereby crystallizes out, advantageously by filtration—the impurities remain in solution here—and then converting the di-alkali metal salt of NTC into free NTC or free NTC-1,8-monoanhydride by treatment with a strong acid at 20°-100° C.

Specifically, the process is advantageously carried out by dissolving the impure NTC or the impure NTC-1,8-monoanhydride in 10 to 50 times, preferably 20 to 25 times, the amount of water in the presence of at least the equivalent amount—based on the 4 carboxylic acid groups of the NTC—of an alkali metal carbonate, such as, for example, sodium carbonate or potassium carbonate, or, preferably, an alkali metal hydroxide, such as sodium hydroxide or potassium hydroxide. If no clear solution results here, the mixture is clarified (filtered) if necessary in the presence of a clarifying auxiliary. If the NTC is already obtained in the form of an aqueous solution of its tetra-alkali metal salt in the course of its synthesis process, this solution can be used in the same way as the starting solution for the process according to the invention.

The solution is then brought to a pH value of 4–5 at a temperature below 45° C., preferably at 0°–30° C., by slow addition of a moderately strong to strong acid, preferably a mineral acid, such as, for example hydrochloric acid, sulfuric acid or o-phosphoric acid, whereupon the di-alkali metal salt of NTC crystallizes out. The precipitation can be brought to completion by addition of a small amount of alkali metal salt. The di-alkali metal salt of NTC is separated off, for example by filtration, and then converted into NTC or its 1,8-monoanhydride by introduction into a strong acid, for example a mineral acid, such as, for example, hydrochloric acid, sulfuric acid or o-phosphoric acid.

By di-alkali metal salts of NTC there are chiefly to be understood the dipotassium salt and the disodium salt, the disodium salt being of particular industrial value.

The temperature at which the precipitation of the di-alkali metal salt by acidification to pH 4–5 takes place must be below 45° C. The precipitation is preferably carried out at a temperature of 0°–30° C. Temperatures below 0° C. are also possible, if they are above the solidification point of the mixture. It is also possible to carry out the precipitation of the di-alkali metal salt at 20°–30° C. and only then to cool the suspension to bring the crystallization to completion. Although precipitation and isolation of the di-alkali metal salt of NTC at temperatures between 30° and immediately below 45° C. is possible, it is not particularly advantageous, since the losses in yield during isolation in this temperature range are too high because of the solubility of the di-alkali metal salt.

If the precipitation and isolation of the di-alkali metal salt of NTC are carried out at 20°–30° C., it is advantageous to bring the precipitation to completion by addition of about 5% by weight (based on the volume of the suspension) of alkali metal chloride, whilst no addition of alkali metal chloride is necessary if the isolation of the di-alkali metal salt is carried out at a temperature of 0°–10° C.

On acidification of a solution of the tetra-alkali metal salt of NTC, the di-alkali metal salt of NTC starts to crystallize out in the pH range of 5 to 6. To bring the precipitation to completion, the mixture is acidified to a pH value of 4–5, preferably 4.5–4.8. The di-alkali metal salt is still substantially stable in the suspension down to about pH 3, and is converted into NTC at lower pH values. Any desired acids can be used for the acidification to pH 4–5, but mineral acids, such as hydrochloric acid or o-phosphoric acid, are preferred.

If the pH value is brought to 4–5 not at temperatures below 45° C. but in the temperature range from 45° to 100° C., instead of the di-alkali metal salt of NTC, the di-alkali metal salt of the monoanhydride of NTC (formula IV) is obtained in an increasing amount as the temperature increases, this product having, in comparison with the di-alkali metal salt of NTC, a substantially higher water-solubility.

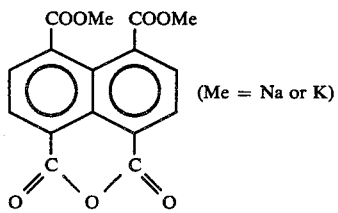

(Me = Na or K)

When the pH value is brought to 4–5 in the temperature range from 80° to 100° C., exclusively the di-alkali metal salt of the monoanhydride of the formula IV is formed. If an aqueous suspension of the di-alkali metal salt of NTC is boiled for a few hours, the salt is likewise substantially converted into the di-alkali metal salt of the monoanhydride of the formula IV. In the same way, the compound of the formula IV is formed if, as is known from examples from the literature, the monoanhydride of NTC is dissolved in water in the presence of two equivalents of alkali metal hydroxide solution.

Whilst the di-alkali metal salt of the monoanhydride of NTC (formula IV) reacts with ammonia to form the di-alkali metal salt of the monoamide of NTC, an attempt to react the di-alkali metal salt of NTC with ammonia gives no such reaction. Furthermore, the di-alkali metal salt of NTC isolated from the aqueous suspension is stable at a higher temperature and can be dried at 100° C. without changing.

The structure of the di-alkali metal salt of NTC is not to be specified, but the structure of the following formula V

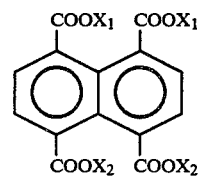

appears to be the most probable, one $X_1$ and one $X_2$ each denoting an alkali metal atom and the other $X_1$ and $X_2$ each denoting a hydrogen atom.

The di-alkali metal salts of NTC are distinguished by characteristic X-ray diffraction spectra which differ substantially from the spectra of the di-alkali metal salts of the monoanhydride of NTC. The X-ray diffraction spectrum of the disodium salt of NTC is characterized by reflexes at diffraction angles ($2\theta$, Cu-K$_\alpha$) of 9.50; 12.85; 14.50; 16.10; 17.25; 20.15; 26.40; 27.60; 28.05; 29.45 and 31.10°, the intensive reflexes at 17.25 and 20.15° being particularly characteristic.

The X-ray diffraction spectrum of the dipotassium metal salt of NTC is characterized by reflexes at diffraction angles ($2\theta$, Cu-K$_\alpha$) of 9.40; 10.90; 13.70; 16.30; 17.90; 19.55; 20.90; 23.35; 26.00; 27.10; 27.75; 29.75 and 30.55°.

If the di-alkali metal salts of NTC are introduced into a dilute aqueous acid, such as, for example, dilute hydrochloric acid, and the mixture is treated at 80°–100°

C. for some time, the monohydride of NTC is obtained in a form which filters so well that a filter cake of monoanhydride with a solids content of 60–80% results on filtration. Because of the low water content, this filter cake can be used directly, without being dried, for the preparation of dyestuffs and pigments.

It is also possible to use the di-alkali metal salts of NTC directly for the preparation of dyestuffs and pigments and thereby to liberate the NTC only in the context of the synthesis. Thus, for example, ®Indanthren-Scharlach GG can be prepared by reacting the disodium salt of NTC with o-phenylenediamine in ethanol in the presence of two equivalents of a strong acid, such as hydrochloric acid or phosphoric acid. In the same way, Indanthren-Scharlach GG can be obtained by condensation by reaction of the disodium salt of NTC with o-phenylenediamine in boiling glacial acetic acid.

The parts and percentages mentioned in the examples are parts by weight and percentages by weight.

EXAMPLE 1

(a) 143 parts of NTC-1,8-monoanhydride of 97% purity are dissolved in a solution of 80 parts of sodium hydroxide in 4000 parts of water at 70°–80° C. The pH is then brought to 4.8–4.5 by dropwise addition of 124 parts of 31% strength hydrochloric acid at 20°–30° C. in the course of 40 minutes, whereupon the disodium salt of NTC precipitates as coarse crystals. The mixture is subsequently stirred at pH 4.8–4.5 for 30 minutes. 200 parts of sodium chloride are then added. The mixture is subsequently stirred at 4.8–4.5 for 2–3 hours, the pH value being adjusted, if necessary, by addition of a small amount of hydrochloric acid. The mixture is then filtered under high suction and the filter cake is rinsed with a little ice-water.

(b) The filter cake obtained according to 1(a) is introduced into a mixture of 1500 parts of water and 150 parts of 31% strength hydrochloric acid at 90°–100° C. and the mixture is subsequently stirred at 90°–100° C. for 1 hour. It is then filtered hot with suction and the filter cake is washed with 1000 parts of 1% strength hydrochloric acid and dried at 100° C. in vacuo. 136 parts of NTC-1,8-monoanhydride of 99–100% purity are obtained.

(c) If the filter cake obtained according to Example 1(a) is dried at 100° C. in vacuo, 166 parts of the disodium salt of NTC are obtained. FIG. 1 shows the X-ray diffraction spectrum (Cu-K$_\alpha$) of this compound. Analysis gives the following sodium value:

calculated (mol 348): 13.2% of sodium. found: 13.1% of sodium.

(d) To prepare Indanthren-Scharlach GG, 104.4 parts of the dry disodium salt of NTC obtained according to Example 1(c) are introduced into a mixture of 500 parts of glacial acetic acid and 500 parts of water together with 70 parts of 1,2-diaminobenzene, and the mixture is boiled under reflux for 6 hours, with thorough stirring. It is then filtered hot with suction and the filter cake is washed with hot water until free from glacial acetic acid and dried at 100° C. in vacuo. 121.7 parts of Indanthren-Scharlach GG are obtained.

EXAMPLE 2

(a) 143 parts of technical grade NTC-1,8-monoanhydride of 91% purity (prepared by oxidation of technical grade 2,7-dibromo-1,2,3,6,7,8-hexahydro-1,3,6,8-pyrenetetrone with nitric acid in sulfuric acid) are dissolved in a solution of 80 parts of sodium hydroxide in 4000 parts of water at 70°–80° C. Insoluble material is removed by filtration. The solution is then brought to pH 4.8–5.0 by dropwise addition of 468 parts of 20% strength ortho-phosphoric acid at 17°–24° C. in the course of 2 hours, whereupon the disodium salt of NTC crystallizes out. After the mixture has been subsequently stirred at 20°–25° C. for 8 hours, it is filtered under a high suction. The filter cake is further processed analogously to Example 1(b). 124 parts of NTC-1,8-monoanhydride of 99–100% purity are obtained.

(b) If the solution of the tetrasodium salt of NTC is brought to pH 4.8–5.0 at 90°–100° C. instead of at 17°–24° C. and the mixture is then cooled to 20°–25° C. and subsequently stirred at 20°–25° C. for 8 hours, a product likewise crystallizes out, which is essentially the disodium salt of NTC-1,8-monoanhydride. If the precipitated product is isolated by filtration and further processed analogously to Example 2(a), only 85 parts of NTC-1,8-monoanhydride are obtained.

EXAMPLE 3

(a) 143 parts of technical grade NTC-1,8-monoanhydride of 92% purity (prepared by oxidation of technical grade, approximately 90% pure 2,7-dibromo-1,2,3,6,7,8-hexahydro-1,3,6,8-pyrenetetrone with hypochlorite solution in dilute sodium hydroxide solution and subsequent precipitation of the NTC with hydrochloric acid) are dissolved in a solution of 80 parts of sodium hydroxide in 3000 parts of water at 70°–80° C. The pH is then brought to 4.8–4.5 by dropwise addition of 124 parts of 31% strength hydrochloric acid at 20°–30° C. in the course of 70 minutes, with thorough stirring, whereupon the disodium salt of NTC crystallizes out. After the mixture has been subsequently stirred for 1 hour, 100 parts of sodium chloride are added. Stirring is then continued at 20°–30° C. and pH 4.8–4.5 for 8 hours. Finally, the mixture is filtered with a high suction. The filter cake is further processed analogously to Example 1(b). 128.5 parts of NTC-1,8-monoanhydride of 99–100% purity are obtained.

(b) If only 2000 parts of water are used for dissolving the NTC-1,8-monoanhydride instead of 3000 parts, the addition of sodium chloride can be omitted before isolation of the disodium salt of NTC. In this case, 129 parts of NTC-1,8-monoanhydride of 98.5–99% purity are obtained.

EXAMPLE 4

(a) 4500 parts of an aqueous solution, which is rendered slightly alkaline with sodium hydroxide solution and contains sodium chloride, and, besides soluble impurities, contains 196 parts of the tetrasodium salt of NTC (prepared by oxidation of technical grade approximately 90% pure 2,7-dibromo-1,2,3,6,7,8-hexahydro-1,3,6,8-pyrenetetrone in dilute sodium hydroxide solution with hypochlorite solution), are brought to pH 5.0–4.5 by dropwise addition of 161 parts of 31% strength hydrochloric acid at 20°–30° C. in the course of 45 minutes, with thorough stirring, whereupon the disodium salt of NTC crystallizes out as coarse crystals. 150 parts of sodium chloride are then added and the mixture is subsequently stirred at 20°–30° C. for 2–3 hours, the pH being monitored. After filtration with a high suction, the filter cake is introduced into 1500 parts of water. The mixture is then heated to 90°–100° C. 200 parts of 31% strength hydrochloric acid are then added dropwise at 90°–100° C. The mixture is then again subsequently stirred at 90°–100° C. for 1 hour and filtered off hot with suction and the filter cake is washed with 1000 parts of 0.5% strength hydrochloric acid and finally dried at 100° C. in vacuo. 139 parts of NTC-1,8-monohydride of 98–99% purity are obtained.

(b) If the starting solution in Example 4a is acidified to pH 1 directly with hydrochloric acid at 20°–30° C. and then stirred at 90°–100° C. for 1 hour and the product is isolated analogously to Example 4a, NTC-1,8-monoanhydride of only 91% purity is obtained.

EXAMPLE 5

143 parts of technical grade NTC-1,8-monoanhydride of 92% purity are dissolved in a solution of 80 parts of sodium hydroxide in 3000 parts of water at 70°–80° C., and the solution is filtered. The solution is then cooled to 0°–5° C. Thereafter, the pH is brought to 4.5–5 by dropwise addition of 126 parts of 31% strength hydrochloric acid at 0°–5° C. in the course of 30 minutes, with thorough stirring, whereupon the disodium salt of NTC crystallizes out. After the mixture has been subsequently stirred at 0°–5° C. for 1 hour, it is filtered with a high suction, the filter cake is introduced into 1500 parts of hot water and the mixture is brought to pH 1.5 with 31% strength hydrochloric acid at 90°–100° C. The mixture is then again subsequently stirred at 90°–100° C. for 1 hour. Finally, it is filtered hot with suction and the filter cake is washed with a little water until free from salts and dried at 100° C. in vacuo. 130 parts of NTC-1,8-monoanhydride of 99% purity are obtained.

EXAMPLE 6

(a) 143 parts of NTC-1,8-monoanhydride of 92% purity are dissolved in a solution of 130 parts of 85% pure potassium hydroxide in 3000 parts of water at 70°–80° C. The pH is then brought to 4.8–4.5 by slow addition of 130 parts of 31% strength hydrochloric acid at 20°–30° C. in the course of 40 minutes. 100 parts of potassium chloride are then added. After the mixture has been subsequently stirred at 20°–30° C. for 3 hours, it is filtered with a high suction.

(b) If the filter cake obtained according to Example 6(a) is further processed according to Example 1(b), 172 parts of NTC-1,8-monoanhydride of 98–99% purity are obtained.

(c) If the filter cake obtained according to Example 6(a) is washed with a little ice-water and then dried at 100° C., 166 parts of the dipotassium salt of NTC are obtained. FIG. 2 shows the X-ray diffraction spectrum (Cu-K$_\alpha$) of this compound.

We claim:

1. A process for the preparation of naphthalene-1,4,5,8-tetracarboxylic acid (called "NTC" below) and its 1,8-monoanhydride in a high degree of purity, which comprises dissolving impure NTC or impure NTC-1,8-monoanhydride (the impurities contained in the said two starting materials originating from their preparation from pyrene) in water under the addition of at least the stoichiometric amount of alkali metal hydroxide as the tetra-alkali metal salt of NTC in water, removing any insoluble impurities present, bringing the clarified solution to a pH value of 4–5 below 45° C., separating off the di-alkali metal salt of NTC which thereby crystallizes out and converting the latter into free NTC or free NTC-1,8-monoanhydride by treatment with a strong acid at 20° to 100° C.

2. The process as claimed in claim 1, wherein the pH of the clarified aqueous solution of the tetra-alkali metal salt of NTC is brought to the value of 4–5 by means of hydrochloric acid, sulfuric acid or o-phosphoric acid.

3. The process as claimed in claim 1, wherein the pH value is brought to 4–5 at a temperature of 0° to 30° C.

4. The process as claimed in claim 1, wherein the clarified aqueous solution of the tetra-alkali metal salt of NTC is brought to a pH value of 4.5–4.8.

5. The process as claimed in claim 1, wherein the di-alkali metal salt of NTC which has been separated off is converted into free NTC or into free NTC-1,8-monoanhydride by introduction of the di-alkali metal salt of NTC into hydrochloric acid, sulfuric acid or o-phosphoric acid.

6. The process as claimed in claim 1, wherein an aqueous solution of the tetrasodium salt of naphthalene tetracarboxylic acid obtained by alkaline oxidation of 1,2,3,6,7,8-hexahydro-1,3,6,8-pyrenetetrone or 2,7-dibromo-1,2,3,6,7,8-hexahydro-1,3,6,8-pyrenetetrone, is used as the starting material.

7. The disodium salt of naphthalene tetracarboxylic acid, which has an X-ray diffraction spectrum with reflexes at diffraction angles (2θ, Cu-K$_\alpha$) of 9.50; 12.85; 14.50; 16.10; 17.25; 20.15; 26.40; 27.60; 28.05; 29.45 and 31.10°.

8. The dipotassium salt of naphthalene tetracarboxylic acid, which has an X-ray diffraction spectrum with reflexes at diffraction angles (2θ, Cu-K$_\alpha$) of 9.40; 10.90; 13.70; 16.30; 17.90; 19.55; 20.90; 23.35; 26.00; 27.10; 27.75; 29.75 and 30.55°.

* * * * *